United States Patent [19]
Ellis et al.

[11] Patent Number: 5,955,309
[45] Date of Patent: Sep. 21, 1999

[54] POLYNUCLEOTIDE ENCODING G-PROTEIN COUPLED RECEPTOR (H7TBA62)

[75] Inventors: Catherine E Ellis, Glassboro, N.J.; Ganesh M Sathe, King of Prussia, Pa.

[73] Assignee: Smithkline Beecham Corporation, Philadelphia, Pa.

[21] Appl. No.: 08/958,240

[22] Filed: Oct. 27, 1997

Related U.S. Application Data

[60] Provisional application No. 60/050,122, Jun. 18, 1997.

[51] Int. Cl.$^6$ .............................. C12N 15/12; C12N 5/10; C12N 15/63; C07K 14/705
[52] U.S. Cl. .................... 435/69.1; 536/23.1; 536/23.5; 536/24.3; 536/24.31; 435/71.2; 435/252.3; 435/320.1; 435/470; 435/254.11; 435/325
[58] Field of Search ................................ 435/69.1, 7.1, 435/7.2, 252.3, 320.1, 471, 325, 254.11; 536/23.4, 23.1, 23.5, 24.3, 24.31; 530/350

[56] References Cited

U.S. PATENT DOCUMENTS

| | | | |
|---|---|---|---|
| 5,556,780 | 9/1996 | Dzau et al. | 435/240.2 |
| 5,591,620 | 1/1997 | Musters et al. | 435/201 |

OTHER PUBLICATIONS

George et al. Macromolecular Sequencing and Synthesis, Selected Methods and Applications, Alan R. Liss, Inc., Chptr. 12, pp. 127–149,1988.

GenBank Accession #P31391 Jul. 1, 1993. Xu et al.

GenBank Accession #P25106 May 1, 1992 Sacedhanan et al.

GenBank Accession #L07062 Aug. 20, 1993 Connen et al.

GenBank Accession #U03642 June 11, 1996 O'Dowd et al.

EST #1463525, Mar. 19, 1997.

*Primary Examiner*—Prema Mertz
*Attorney, Agent, or Firm*—Elizabeth J. Hecht; Ratner & Prestia; William T. King

[57] ABSTRACT

H7TBA62 polypeptides and polynucleotides and methods for producing such polypeptides by recombinant techniques are disclosed. Also disclosed are methods for utilizing H7TBA62 polypeptides and polynucleotides in the design of protocols for the treatment of infections such as bacterial, fungal protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others and diagnostic assays for such conditions.

36 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3748 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GAGCTCTGTC CACAGACTAG AGCAGGAAAG GGGGGAAAGG CGGCGATAGA GGTTAGCAGG      60

AATGTTTAAT TATCAGGAGC AGGAACAGAA CTGAGGGCAT GCCCAGGTCC ACACAGGCCC     120

TCATAGGCCC AGTGTTCCCA GTGGGGAGGA AACAGGAAGC TGTGACTTCC TCTCTCTTTT     180

CCCTCCCTGC TCTTAGCCTC AAGGTCACTG CTGCTGAGAT GAATTCCAAC CTGTTTTAGT     240
```

```
TGGCACTGTT CCCTGGGCAT GGTAATAGCC TCTCAGTACC CTTCTGCCAC AAACACCCCA    300

AACTTCTCCT TTGAAATAAT ATTCATACAA ATTGCTATTT CACATGTATT CTCTCATTGC    360

ATCATGCCAC TCCTGTGAAG CAGACTTACC TGAAAATTTT AAGCAAGAAA ACAGGCTTAG    420

GGGAGTAAAG TAACTCTCCC AGTCACACGG CTAGTGAGCA GCAGGTCTGG GACTCCGCAG    480

CCTCCGCTCT TTCCTCTCTT GGACACCCAT GCTGATTCCC TGCCTCTATG CCACCTCCCA    540

GGCCCCTTGC TTTGGGCCCC AAGGGAACAC TTTTTGCAGA GGAGGGAGGC CTCTGCACTG    600

TTAGGAACAG AGGCAGCTCT AGTTTGGTTC CTGTCATCTC TGGGACAGGG AAACCTCCAG    660

CTCTCTCCCT GGGGTGGAGG CTTGGGGCTG CCCTCCATAG CGGGGTAACT CTCCCTTCTC    720

CCCTCCCTCT CTGCCATTTA GAGCCCCTCT TACAGGCGGG CGCATGCACA TATACCCTGG    780

CATTCAGGCT GTGCCTCGCC CTGCCCCACC TACCACCAAT CTTGACCAAC AGGAAGGTGG    840

TGGGTTGTCC TTTCCACACC CCTCCCTCTG AGGTGTGGGC GTGGGCCAGG GCTCACCAGA    900

GGCCCCAGAG AAGCACTTAA TTCTACAGCC TCCTTCCTAG AGCCTTCAGT GGCCTCTGCC    960

AGTCTGGCAG ACACTTGCAG ACCTCTCTTC TCAGCACCAC CAATCTCTGA TGCCCTGCGA    1020

TGCCCACACT CAATACTTCT GCCTCTCCAC CCACATTCTT CTGGGCCAAT GCCTCCGGAG    1080

GCAGTGTGCT GAGTGCTGAT GATGCTCCGA TGCCTGTCAA ATTCCTAGCC CTGAGGCTCA    1140

TGGTTGCCCT GGCCTATGGG CTTGTGGGGG CCATTGGCTT GCTGGGAAAT TTGGCGGTGC    1200

TGTGGGTACT GAGTAACTGT GCCCGGAGAG CCCCTGGCCC ACCTTCAGAC ACCTTCGTCT    1260

TCAACCTGGC TCTGGCGGAC CTGGGACTGG CACTCACTCT CCCCTTTTGG GCAGCCGAGT    1320

CGGCACTGGA CTTTCACTGG CCCTTCGGAG GTGCCCTCTG CAAGATGGTT CTGACGGCCA    1380

CTGTCCTCAA CGTCTATGCC AGCATCTTCC TCATCACAGC GCTGAGCGTT GCTCGCTACT    1440

GGGTGGTGGC CATGGCTGCG GGGCCAGGCA CCCACCTCTC ACTCTTCTGG GCCCGAATAG    1500

CCACCCTGGC AGTGTGGGCG GCGGCTGCCC TGGTGACGGT GCCCACAGCT GTCTTCGGGG    1560

TGGAGGGTGA GGTGTGTGGT GTGCGCCTTT GCCTGCTGCG TTTCCCCAGC AGGTACTGGC    1620

TGGGGGCCTA CCAGCTGCAG AGGGTGGTGC TGGCTTTCAT GGTGCCCTTG GGCGTCATCA    1680

CCACCAGCTA CCTGCTGCTG CTGGCCTTCC TGCAGCGGCG GCAACGGCGG CGGCAGGACA    1740

GCAGGGTCGT GGCCCGCTCT GTCCGCATCC TGGTGGCTTC CTTCTTCCTC TGCTGGTTTC    1800

CCAACCATGT GGTCACTCTC TGGGGTGTCC TGGTGAAGTT TGACCTGGTG CCCTGGAACA    1860

GTACTTTCTA TACTATCCAG ACGTATGTCT TCCCTGTCAC TACTTGCTTG GCACACAGCA    1920

ATAGCTGCCT CAACCCTGTG CTGTACTGTC TCCTGAGGCG GGAGCCCCGG CAGGCTCTGG    1980

CAGGCACCTT CAGGGATCTG CGGTCGAGGC TGTGGCCCCA GGGCGGAGGC TGGGTGCAAC    2040

AGGTGGCCCT AAAGCAGGTA GGCAGGCGGT GGGTCGCAAG CAACCCCCGG GAGAGCCGCC    2100

CTTCTACCCT GCTCACCAAC CTGGACAGAG GGACACCCGG GTGAAGGGCG CAAGCTGAAC    2160

ACACTCCTCT TTCTGAGATC CACCAAGTGT AGGATCCTTG AGTCCTGGGG AGAAGCTGCC    2220

CTCTCTGCCA GGCTGCAGTG CCCTCAGGGA AAAAGTCTGA TCTTTGATCC CCAACTCTGG    2280

GTGTGGTGAA TGGGGGAGGC GGGGGCTCAG ATCAGAGCTG GATGTGACAA AGCTTAAGTC    2340

TTTATTTGGA GATGGGAAAG AAGAGGATCT GAGAATAAAC CTCTGGATTA TCCACAAATT    2400

GTCTTGACCT TTTATCCCAG TTCCACCTCC AGTTCAGTAT GGAACAAAAG GATTCGTTGC    2460

TCCATTTCTG CTTTCGCAAG AATACCTAGG AAAACTTCCC TAAGGGTTCT AGGCTAATGA    2520

ATCAGAGGTC AGTGCCCATC TCTCTCTGTA CCCACCCCCC ACCTCAAAAC AGGGTATCCC    2580

TTGTCTTTCT CCGGTATCAA GGCCAAAAAT GCCAGCTTCC CCTGTCCTCA CCTTACCATC    2640
```

```
TCAGTGGTGA CCACTGAAAC TTGCTGCCTG CAGAGGCCTC AGCTGCAAAA GCTGTAGTTC      2700

CCTTGAAGGG ATGCCAGGTG TGGGGTATTG CTGGAATTTC CAGCACCTGC CAGGCCCTGG      2760

GTGTAAAACC CTGGTGCTGA CGGGAGTGCC TGTGTGTCTC CCTCTAAATC AGGATTTGAA      2820

AGAAGTGAAG ATAATGACAA GTCAAAGACA TGGGTGGGGT GAAGGGAGGT GAGCGATTAA      2880

AGAGGGGAGG GGGCTGGGAG AACAGGCTGC AGGTAGAGCC AGAAAAGCAG AGACTCCAGA      2940

AAGTGGTGCT AGTCCTCCCT GCCCCAAATG CAAAGCCCAG AGTATCAATT TGAGTGTCAG      3000

AGCACCTGGA TTCACAGCTT TACCTCCAGC AAATTACTTT ACCTCTTTGT ACCTCACTGT      3060

TCTCAACTGT AAAATGGGCT ACTAAAGATT TAACAGTGAA ATATACTGTT AGCTATTATT      3120

CTTGTTTGTT TGTTTGTTTG TTTGAGACAG AGTCTCGTTC TGTCGCCCAG GCTGGAGTGC      3180

AGTGGTGTGA TCTCAGCTCA CTGCAACCTC CGCTTCCCGG GTTCAAGCGA TTCTCCTGCC      3240

TCAGCCTCCC GAGTAGCTGG GACTACAGGC TCCCGCTACC ATGCCTGGCC AATTTTTTGT      3300

AATTTTTAAT AGAGACAGAG TTTCACCATA TTGGCCAGGC TGGTCTCAAA CTCCTGACCT      3360

CTAGTGATCT GCCCACCTCG GCCTCCCAAA GTGCTGGAGT TACAGGCGTG AGCCACCGCA      3420

CCCGGTCGAG CTATTATTCT TACACCCTGT GTAAAATGGA GACAGAGAGA TGGGAGGAAA      3480

TAAGCGTGCA GCTGGGAGAT GGGGATGGGG AACCATGTCT CAGCTGGAAT GGTTGTATAT      3540

GCTCTGAAGT GGGGTATAAT GAAAGTCTCA CATAAAGAAC TCAGAGGTTG GCCCCTAAGC      3600

CCCTCTTGAA GGTGTGTTCT CCAGGACAGG GGTTCCTCTT TGGTTCCTGT ATTGAGATGC      3660

ATCAATGATA AAGGTTAGCC ATCAGAAGGA TTTTCTAGGA GGCAGCCCCT AGAAAGGAGG      3720

GAGGCAGAGG GAAGATGAGG TAGAGCTC                                        3748
```

(2) INFORMATION FOR SEQ ID NO:2:

(i) SEQUENCE CHARACTERISTICS:
        (A) LENGTH: 374 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Pro Thr Leu Asn Thr Ser Ala Ser Pro Thr Phe Phe Trp Ala
 1               5                  10                  15

Asn Ala Ser Gly Gly Ser Val Leu Ser Ala Asp Asp Ala Pro Met Pro
                20                  25                  30

Val Lys Phe Leu Ala Leu Arg Leu Met Val Ala Leu Ala Tyr Gly Leu
            35                  40                  45

Val Gly Ala Ile Gly Leu Leu Gly Asn Leu Ala Val Leu Trp Val Leu
        50                  55                  60

Ser Asn Cys Ala Arg Arg Ala Pro Gly Pro Ser Asp Thr Phe Val
65                  70                  75                  80

Phe Asn Leu Ala Leu Ala Asp Leu Gly Leu Ala Leu Thr Leu Pro Phe
                85                  90                  95

Trp Ala Ala Glu Ser Ala Leu Asp Phe His Trp Pro Phe Gly Gly Ala
               100                 105                 110

Leu Cys Lys Met Val Leu Thr Ala Thr Val Leu Asn Val Tyr Ala Ser
           115                 120                 125

Ile Phe Leu Ile Thr Ala Leu Ser Val Ala Arg Tyr Trp Val Val Ala
       130                 135                 140

Met Ala Ala Gly Pro Gly Thr His Leu Ser Leu Phe Trp Ala Arg Ile
```

```
            145                 150                 155                 160
Ala Thr Leu Ala Val Trp Ala Ala Ala Leu Val Thr Val Pro Thr
                    165                 170                 175
Ala Val Phe Gly Val Glu Gly Glu Val Cys Gly Val Arg Leu Cys Leu
                180                 185                 190
Leu Arg Phe Pro Ser Arg Tyr Trp Leu Gly Ala Tyr Gln Leu Gln Arg
            195                 200                 205
Val Val Leu Ala Phe Met Val Pro Leu Gly Val Ile Thr Thr Ser Tyr
        210                 215                 220
Leu Leu Leu Leu Ala Phe Leu Gln Arg Gln Arg Arg Arg Gln Asp
225                 230                 235                 240
Ser Arg Val Val Ala Arg Ser Val Arg Ile Leu Val Ala Ser Phe Phe
                245                 250                 255
Leu Cys Trp Phe Pro Asn His Val Val Thr Leu Trp Gly Val Leu Val
                260                 265                 270
Lys Phe Asp Leu Val Pro Trp Asn Ser Thr Phe Tyr Thr Ile Gln Thr
                275                 280                 285
Tyr Val Phe Pro Val Thr Thr Cys Leu Ala His Ser Asn Ser Cys Leu
        290                 295                 300
Asn Pro Val Leu Tyr Cys Leu Arg Arg Glu Pro Arg Gln Ala Leu
305                 310                 315                 320
Ala Gly Thr Phe Arg Asp Leu Arg Ser Arg Leu Trp Pro Gln Gly Gly
                325                 330                 335
Gly Trp Val Gln Gln Val Ala Leu Lys Gln Val Gly Arg Arg Trp Val
                340                 345                 350
Ala Ser Asn Pro Arg Glu Ser Arg Pro Ser Thr Leu Leu Thr Asn Leu
                355                 360                 365
Asp Arg Gly Thr Pro Gly
370
```

(2) INFORMATION FOR SEQ ID NO:3:

(i) SEQUENCE CHARACTERISTICS:
        (A) LENGTH: 739 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
CGGCCGCCAG TGTGATGGAT ATCTGCAGAA TTCGGCTTAT CGTGAACCTG GCTTTGGTGG      60
ACCTGGGACT GGCACTCACT CTCCCCTTTT GGGCAGCCGA GTCGGCACTG GACTTTCACT     120
GGCCCTTCGG AGGTGCCCTC TGCAAGATGG TTCTGACGGC CACTGTCCTC AACGTCTATG     180
CCAGCATCTT CCTCATCACA GCGCTGAGCG TTGCTCGCTA CTGGGTGGTG GCCATGGCTG     240
CGGGGCCAGG CACCCACCTC TCACTCTTCT GGGCCCGAAT AGCCACCCTG GCAGTGTGGG     300
CGGCAGCTGC CCTGGTGACG GTGCCCACAG CTGTCTTCGG GGTGGAGGGT GAGGTGTGTG     360
GTGTGCGCCT TTGCCTGCTG CGTTTCCCCA GCAGGTACTG GCTGGGGGCC TACCAGCTGC     420
AGAGGGTGGT GCTGGCTTTC ATGGTGCCCT TGGGCGTCAT CACCACCAGC TACCTGCTGC     480
TGCTGGCCTT CCTGCAGCGG CGGCAACGGC GGCGGCAGGA CAGCAGGGTC GTGGCCCGCT     540
CTGTCCGCAT CCTGGTGGCT TCCTTCTTCC TCTGCTGGTT TCCCAACCAT GTGGTCACTC     600
TCTGGGGTGT CCTGGTGAAG TTTGACCTGG TGCCCCTGGA ACAGTACTTT CTATACTATC     660
CAGACGTATG TCTTCCCTGT CACTACTTGC TTGGCACACA GCAATAGCTG TCTCAACCCA     720
```

TTTGCCTATG TCTTAAGCC                                                    739

(2) INFORMATION FOR SEQ ID NO:4:

(i) SEQUENCE CHARACTERISTICS:
        (A) LENGTH: 234 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Ala Ala Ser Val Met Asp Ile Cys Arg Ile Arg Leu Ile Val Asn Leu
1               5                   10                  15

Ala Leu Val Asp Leu Gly Leu Ala Leu Thr Leu Pro Phe Trp Ala Ala
                20                  25                  30

Glu Ser Ala Leu Asp Phe His Trp Pro Phe Gly Gly Ala Leu Cys Lys
            35                  40                  45

Met Val Leu Thr Ala Thr Val Leu Asn Val Tyr Ala Ser Ile Phe Leu
        50                  55                  60

Ile Thr Ala Leu Ser Val Ala Arg Tyr Trp Val Val Ala Met Ala Ala
65                  70                  75                  80

Gly Pro Gly Thr His Leu Ser Leu Phe Trp Ala Arg Ile Ala Thr Leu
                85                  90                  95

Ala Val Trp Ala Ala Ala Ala Leu Val Thr Val Pro Thr Ala Val Phe
                100                 105                 110

Gly Val Glu Gly Glu Val Cys Gly Val Arg Leu Cys Leu Leu Arg Phe
            115                 120                 125

Pro Ser Arg Tyr Trp Leu Gly Ala Tyr Gln Leu Gln Arg Val Val Leu
        130                 135                 140

Ala Phe Met Val Pro Leu Gly Val Ile Thr Thr Ser Tyr Leu Leu Leu
145                 150                 155                 160

Leu Ala Phe Leu Gln Arg Arg Gln Arg Arg Gln Asp Ser Arg Val
                165                 170                 175

Val Ala Arg Ser Val Arg Ile Leu Val Ala Ser Phe Phe Leu Cys Trp
            180                 185                 190

Phe Pro Asn His Val Val Thr Leu Trp Gly Val Leu Val Lys Phe Asp
        195                 200                 205

Leu Val Pro Leu Glu Gln Tyr Phe Leu Tyr Tyr Pro Asp Val Cys Leu
    210                 215                 220

Pro Cys His Tyr Leu Leu Gly Thr Gln Gln
225                 230

POLYNUCLEOTIDE ENCODING G-PROTEIN COUPLED RECEPTOR (H7TBA62)

This application claims the benefit of U.S. Provisional Application No. 60/050,122, filed Jun. 18, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to G-protein coupled receptor family, hereinafter referred to as H7TBA62. The invention also relates to inhibiting or activating the action of such polynucleotides and polypeptides.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone biding is activation of the enzyme, adenylate cyclase, inside the cell. Enzyme activation by hormones is dependent on the presence of the nucleotide, GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetycholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said sockets being by surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331). Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7 TM) receptors have been successfully introduced onto the market.

This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to H7TBA62 polypeptides and recombinant materials and methods for their production. Another aspect of the invention relates to methods for using such H7TBA62 polypeptides and polynucleotides. Such uses include the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with H7TBA62 imbalance with the identified compounds. Yet another aspect of the invention relates to diagnostic assays for detecting diseases associated with inappropriate H7TBA62 activity or levels.

DESCRIPTION OF THE INVENTION

Definitions

The following definitions are provided to facilitate understanding of certain terms used frequently herein.

"H7TBA62" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said H7TBA62 including similar activities or improved activities or these activities with decreased undesirable side-effects. Also included are antigenic and immunogenic activities of said H7TBA62.

"H7TBA62 gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to H7TBA62 polypeptides (or H7TBA62 proteins). The H7TBA62 polypeptides include the polypeptides of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within H7TBA62 polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably H7TBA62 polypeptides exhibit at least one biological activity of the receptor.

The H7TBA62 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the H7TBA62 polypeptides are also included in the invention. A fragment is a polypeptide having an amino acid sequence that entirely is the same as part, but not all, of the amino acid sequence of the aforementioned H7TBA62 polypeptides. As with H7TBA62 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of H7TBA62 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of H7TBA62 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The H7TBA62 polypeptides of the invention can be prepared in any suitable manner. Such polypeptides include isolated naturally occurring polypeptides, recombinantly produced polypetides, synthetically produced polypeptides, or polypeptides produced by a combination of these methods. Means for preparing such polypeptides are well understood in the art.

Polynucleotides of the Invention

Another aspect of the invention relates to H7TBA62 polynucleotides. H7TBA62 polynucleotides include isolated polynucleotides which encode the H7TBA62 polypeptides and fragments, and polynucleotides closely related. More specifically, H7TBA62 polynucleotide of the invention include a polynucleotide comprising the nucleotide sequence contained in SEQ ID NO:1 encoding a H7TBA62 polypeptide of SEQ ID NO: 2, and polynucleotides having the particular sequences of SEQ ID NOS:1 and 3. H7TBA62 polynucleotides further include a polynucleotide comprising a nucleotide sequence that has at least 80% identity over its entire length to a nucleotide sequence encoding the H7TBA62 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under H7TBA62 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such H7TBA62 polynucleotides.

H7TBA62 of the invention is structurally related to other proteins of the G-protein coupled receptor family, as shown by the results of sequencing the cDNA encoding human H7TBA62. The cDNA sequence of SEQ ID NO:1 contains an open reading frame (nucleotide number 1020 to 2141) encoding a polypeptide of 374 amino acids of SEQ ID NO:2. The amino acid sequence of Table 1 (SEQ ID NO:2) has about 32% identity (using FASTA) in 300 amino acid residues with Human Somatostatin Receptor Type 4 (PNAS 90:4196–4200, 1993). Furthermore, H7TBA62 (SEQ ID NO: 2) is 27% identical to the Human RDC-1 homolog Receptor over 318 amino acid residues (PNAS 88:4986–4990, 1991). The nucleotide sequence of Table 1 (SEQ ID NO:1) has about 55% identity (using FASTA) in 1079 nucleotide residues with Human Somatostatin Receptor Type 3 (FEBS Lett. 321,279–284, 1993). Furthermore, H7TBA62 (SEQ ID NO: 1) is 56% identical to Human APJ Receptor over 596 nucleotide base residues (Gene 136, 355–360, 1993). Thus, H7TBA62 polypeptides and polynucleotides of the present invention are expected to have, inter alia, similar biological functions/properties to their homologous polypeptides and polynucleotides, and their utility is obvious to anyone skilled in the art.

TABLE 1$^a$

| | | | | | |
|---|---|---|---|---|---|
| 1 | GAGCTCTGTC | CACAGACTAG | AGCAGGAAAG | GGGGGAAAGG | CGGCGATAGA |
| 51 | GGTTAGCAGG | AATGTTTAAT | TATCAGGAGC | AGGAACAGAA | CTGAGGGCAT |
| 101 | GCCCAGGTCC | ACACAGGCCC | TCATAGGCCC | AGTGTTCCCA | GTGGGGAGGA |
| 151 | AACAGGAAGC | TGTGACTTCC | TCTCTCTTTT | CCCTCCCTGC | TCTTAGCCTC |
| 201 | AAGGTCACTG | CTGCTGAGAT | GAATTCCAAC | CTGTTTTAGT | TGGCACTGTT |
| 251 | CCCTGGGCAT | GGTAATAGCC | TCTCAGTACC | CTTCTGCCAC | AAACACCCCA |
| 301 | AACTTCTCCT | TTGAAATAAT | ATTCATACAA | ATTGCTATTT | CACATGTATT |
| 351 | CTCTCATTGC | ATCATGCCAC | TCCTGTGAAg | CAGACTTACC | TGAAAATTTT |
| 401 | AAGCAAGAAA | ACAGGCTTAg | GGGAgTAAAg | TAACTCTCCC | AGTCACACGG |
| 451 | CTAGTGAGCA | GCAGGTCTGG | GACTCCGCAG | CCTCCGCTCT | TTCCTCTCTT |
| 501 | GGACACCCAT | GCTGATTCCC | TGCCTCTATG | CCACCTCCCA | GGCCCCTTGC |
| 551 | TTTGGGCCCC | AAGGGAACAC | TTttTGCAGA | GGAGGGAGGC | CTCTGCACTG |
| 601 | TTAGGAACAG | AGGCAGCTCT | AGTTTGGTTC | CTGTCATCTC | TGGGACAgGG |
| 651 | AAACCTCCAG | CTCTCTCCCT | GGGGTGGAgG | CTTGGGGCTG | CCCTCCATAg |
| 701 | CGGGGTAACT | CTCCCTTCTC | CCCTCCCTCT | CTGCCATTTA | GAGCCCTCT |

TABLE 1[a-continued]

```
 751  TACAGGCGGG CGCATGCACa TATACCCTGG CATTCAgGCT GTGCCTCGCC
 801  CTGCCCCACC TACCACCAAT CTTGACCAAC AGGAAGGTGG TGGGTTGTCC
 851  TTTCCACACC CCTCCCTCTG AGGTGTGGGC GTGGGCCAGG GCTCACCAGA
 901  GGCCCCAGAG AAGCACTTAA TTCTACAGCC TCCTTCCTAG AGCCTTCAGT
 951  GGCCTCTGCC AGTCTGGCAG ACACTTGCAG ACCTCTCTTC TCAGCACCAC
1001  CAATCTCTGA TGCCCTGCGA TGCCCACACT CAATACTTCT GCCTCTCCAC
1051  CCACATTCTT CTGGGCCAAT GCCTCCGGAG GCAGTGTGCT GAGTGCTGAT
1101  GATGCTCCGA TGCCTGTCAA ATTCCTAGCC CTGAGGCTCA TGGTTGCCCT
1151  GGCCTATGGG CTTGTGGGGG CCATTGGCTT GCTGGGAAAT TTGGCGGTGC
1201  TGTGGGTACT GAGTAACTGT GCCCGGAGAG CCCCTGGCCC ACCTTCAGAC
1251  ACcTTCGTCT TCAACCTGGC TCTGGCGGAC CTGGGAcTGG CACTCACTCT
1301  CCCCTTTTGG GCAGCCGAGT CGGCACTGGA CTTTCACTGG CCCTTCGGAG
1351  GTGCCCTCTG CAAGATGGTT CTGACGGCCA CTGTCCTCAA CGTCTATGCC
1401  AGCATCTTCC TCATCACAGC GCTGAGCGTT GCTCGCTACT GGGTGGTGGC
1451  CATGGCTGCG GGGCCAGGCA CCCACCTCTC ACTCTTCTGG GCCCGAATAG
1501  CCACCCTGGC AGTGTGGGCG GCGGCTGCCC TGGTGACGGT GCCCACAGCT
1551  GTCTTCGGGG TGGAGGGTGA GGTGTGTGGT GTGCGCCTTT GCCTGCTGCG
1601  TTTCCCCAGC AGGTACTGGC TGGGGCCTA CCAGCTGCAG AGGGTGGTGC
1651  TGGCTTTCAT GGTGCCCTTG GGCGTCATCA CCACCAGCTA CCTGCTGCTG
1701  CTGGCCTTCC TGCAGCGGCG GCAACGGCGG CGGCAGGACA GCAGGGTCGT
1751  GGCCCGCTCT GTCCGCATCC TGGTGGCTTC CTTCTTCCTC TGCTGGTTTC
1801  CCAACCATGT GGTCACTCTC TGGGGTGTCC TGGTGAAGTT TGACCTGGTG
1851  CCCTGGAACA GTACTTTCTA TACTATCCAg ACGTATGTCT TCCCTGTCAC
1901  TACTTGCTTG GCACACAGCA ATAGCTGCCT CAACCCTGTG CTGTACTGTC
1951  TCCTGAGGCG GGAGCCCCGG CAGGCTCTGG CAGGCACCTT CAGGGATCTG
2001  CGGTCGAGGC TGTGGCCCCA GGGCGGAGGC TGGGTGCAAC AGGTGGCCCT
2051  AAAGCAGGTA GGCAGGCGGT GGGTCGCAAG CAACCCCCGG GAGAGCCGCC
2101  CTTCTACCCT GCTCACCAAC CTGGACAGAG GGACACCCGG GTGAAGGGCG
2151  CAAGCTGAAC ACACTCCTCT TTCTGAGATC CACCAAGTGT AGGATCCTTG
2201  AGTCCTGGGG AGAAGCTGCC CTCTCTGCCA GGCTGCAGTG CCCTCAGGGA
2251  AAAAGTCTGA TCTTTGATCC CCAACTCTGG GTGTGGTGAA TGGGGGAGGC
2301  GGGGGCTCAg ATCAGAGCTG GATGTGACAA AGCTTAAGTC TTTATTTGGA
2351  GATGGGAAAG AAGAGGATCT GAgAATAAAC CTCTGGATTA TCCACAAATT
2401  GTCTTGACCT TTTATCCCAG TTCCACcTCC AGTTCAGTAt GGAACAAAAG
2451  GATTCGTTGC TCCATTTcTG cTTTCGCAAG AATACcTAGG AAAAcTTCCc
2501  TAAGGGTTcT AGGCTAATGA ATCAGAGGTC AGTGCCCATc TcTcTCTGtA
2551  CCCACCCCCC ACcTCAAAAC AGGGTATCCc TTGTCTTTcT CCGGTATCAA
2601  GGCCAAAAAT GCCAGCTTCC CCTGTCCTCA CCTTACCATC TCAGTGGTGA
2651  CCAcTGAAAC TTGCTGCCTG CAGAGGCcTC AGCTGCAAAA GCTGTAGTTC
2701  CCTTGAAGGG ATGCCAGGTG TGGGGTATTG CTGGAATTTC CAGCACCTGC
```

TABLE 1[a]-continued

```
2751 CAGGCCCTGG GTGTAAAACC CTGGTGCTGA CGGGAGTGCC TGTGTGTCTC

2801 CCTcTAAATC AGGATTTGAA AGAAGTGAAG ATAATGACAA GTCAAAGACA

2851 TGGGTGGGGT GAAGGGAGGT GAGCGATTAA AGAGGGGAGG GGGCTGGGAG

2901 AACAGGCTGC AGGTAGAGCC AGAAAAGCAG AGACTCCAGA AAGTGGTGCT

2951 AGTCCTCCCT GCCCCAAATG CAAAGCCCAG AGTATCAATT TGAGTGTCAG

3001 AGCACCTGGA TTCACAGCTT TACCTCCAGC AAATTACTTT ACCTCTTTGT

3051 ACCTCACTGT TCTCAACTGT AAAATGGGCT ACTAAAGATT TAACAGTGAA

3101 ATATACTGTT AGCTATTATT CTTGTTTGTT TGTTTGTTTG TTTGAGACAG

3151 AGTCTCGTTC TGTCGCCCAG GCTGGAGTGC AGTGGTGTGA TCTCAGCTCA

3201 CTGCAACCTC CGCTTCCCGG GTTCAAGCGA TTCTCCTGCC TCAGCCTCCC

3251 GAGTAGCTGG GACTACAGGC TCCCGCTACC ATGCCTGGCC AATTTTTTGT

3301 AATTTTTAAT AGAGACAGAG TTTCACCATA TTGGCCAGGC TGGTCTCAAA

3351 CTCCTGACCT CTAGTGATCT GCCCACCTCG GCCTCCCAAA GTGCTGGAGT

3401 TACAGGCGTG AGCCACCGCA CCCGGTCGAG CTATTATTCT tACACCCTGT

3451 GTAAAATGGA GACAGAGAGA TGGGAGGAAA TAAGCGTGCA GCTGGGAGAT

3501 GGGGATGGGG AACCATGTCT CAGCTGGAAT GGTTGTATAT GCTCTGAAGT

3551 GGGGTATAAT GAAAGTCTCA CATAAAGAAC TCAGAGGTTG GCCCCTAAGC

3601 CCCTCTTGAA GGTGTGTTCT CCAGGACAGG GGTTCCTCTT TGGTTCCTGT

3651 ATTGAGATGC ATCAATGATA AAGGTTAGCC ATCAGAAGGA TTTTCTAGGA

3701 GGCAGCCCCT AGAAAGGAGG GAGGCAGAGG GAAGATGAGG TAGAGCTC
```

[a] A nucleotide sequence of a human H7TBA62 (SEQ ID NO: 1).

TABLE 2[b]

| 1 | MPTLNTSASP | PTFFWANASG | GSVLSADDAP | MPVKFLALRL | MVALAYGLVG |
|---|---|---|---|---|---|
| 51 | AIGLLGNLAV | LWVLSNCARR | APGPPSDTFV | FNLALADLGL | ALTLPFWAAE |
| 101 | SALDFHWPFG | GALCKMVLTA | TVLNVYASIF | LITALSVARY | WVVAMAAGPG |
| 151 | THLSLFWARI | ATLAVWAAAA | LVTVPTAVFG | VEGEVCGVRL | CLLRFPSRYW |
| 201 | LGAYQLQRVV | LAEMVPLGVI | TTSYLLLLAF | LQRRQRRRQD | SRVVARSVRI |
| 251 | LVASFFLCWF | PNHVVTLWGV | LVKFDLVPWN | STFYTIQTYV | FPVTTCLAHS |
| 301 | NSCLNPVLYC | LLRREPRQAL | AGTFRDLRSR | LWPQGGGWVQ | QVALKQVGRR |
| 351 | WVASNPRESR | PSTLLTNLDR | GTPG | | |

[b] An amino acid sequence of a human H7TBA62 (SEQ ID NO: 2).

One polynucleotide of the present invention encoding H7TBA62 may be obtained using standard cloning and screening, from a cDNA library derived from mRNA in cells of human brain using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding H7TBA62 polypeptide of SEQ ID NO:2 may be identical to the polypeptide encoding sequence contained in Table 1 (nucleotide number 1020 to 2141 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of H7TBA62 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding H7TBA62 variants comprising the amino acid sequence of H7TBA62 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

nucleotides and may have at least 50 nucleotides. Particularly preferred probes will range between 30 and 50 nucleotides.

In one embodiment, to obtain a polynucleotide encoding H7TBA62 polypeptide, including homologs and orthologs from species other than human, comprises the steps of screening an appropriate library under stingent hybridization conditions with a labeled probe having the SEQ ID NO: 1 or a fragment thereof (including that of SEQ ID NO: 3), and isolating full-length cDNA and genomic clones containing TABLE 3[c]

| 1 | CGGCCGCCAG | TGTGATGGAT | ATCTCGACAA | TTCGGCTTAT | CGTGAACCTG |
|---|---|---|---|---|---|
| 51 | GCTTTGGTGG | ACCTGGGACT | GGCACTCACT | CTCCCCTTTT | GGGCAGCCGA |
| 101 | GTCGGCACTG | GACTTTCACT | GGCCCTTCGG | AGGTGCCCTC | TGCAAGATGG |
| 151 | TTCTGACGGC | CACTGTCCTC | AACGTCTATG | CCAGCATCTT | CCTCATCACA |
| 201 | GCGCTGAGCG | TTGCTCGCTA | CTGGGTGGTG | GCCATGGCTG | CGGGGCCAGG |
| 251 | CACCCACCTC | TCACTCTTCT | GGGCCCGAAT | AGCCACCCTG | GCAGTGTGGG |
| 301 | CGGCAGCTGC | CCTGGTGACG | GTGCCCACAG | CTGTCTTCGG | GGTGGAGGGT |
| 351 | GAGGTGTGTG | GTGTGCGCCT | TTGCCTGCTG | CGTTTCCCCA | GCAGGTACTG |
| 401 | GCTGGGGGCC | TACCAGCTGC | AGAGGGTGGT | GCTGGCTTTC | ATGGTGCCCT |
| 451 | TGGGCGTCAT | CACCACCAGC | TACCTGCTGC | TGCTGGCCTT | CCTGCAGCGG |
| 501 | CGGCAACGGC | GGCGGCAGGA | CAGCAGGGTC | GTGGCCCGCT | CTGTCCGCAT |
| 551 | CCTGGTGGCT | TCCTTCTTCC | TCTGCTGGTT | TCCCAACCAT | GTGGTCACTC |
| 601 | TCTGGGGTGT | CCTGGTGAAG | TTTGACCTGG | TGCCCCTGGA | ACAGTACTTT |
| 651 | CTATACTATC | CAGACGTATG | TCTTCCCTGT | CACTACTTGC | TTGGCACACA |
| 701 | GCAATAGCTG | TCTCAACCCA | TTTGCCTATG | TCTTAAGCC | |

[c]A partial nucleotide sequence of a human H7TBA62 (SEQ ID NO: 3).

TABLE 4[d]

```
  1 AASVMDICRI RLIVNLALVD LGLALTLPFW AAESALDFHW PFGGALCKMV

51 LTATVLNVYA SIFLITALSV ARYWVVAMAA GPGTHLSLFW ARIATLAVWA

101 AAALVTVPTA VFGVEGEVCG VRLCLLRFPS RYWLGAYQLQ RVVLAFMVPL

151 GVITTSYLLL LAFLQRRQRR RQDSRVVARS VRILVASFFL CWFPNHVVTL

201 WGVLVKFDLV PLEQYFLYYP DVCLPCHYLL GTQQ
```

[d] A partial amino acid sequence of a human H7TBA62 (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding H7TBA62 and to isolate cDNA and genomic clones of other genes (including genes encoding homologs and orthologs from species other than human) that have a high sequence similarity to the H7TBA62 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The preset invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, srape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; inset cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as bacloviruses, papova viruses, such as SV40, vaccinia viruses, adenoviruses, fowl pox viruses, pseudorabies virues and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the H7TBA62 polypeptide is to be expressed for use in screening assays, generally, it is preferred that the polypeptide be produced at the surface of the cell. In this event, the cells may be harvested prior to use in the screening assay. If H7TBA62 polypeptide is secreted into the medium, the medium can be recovered in order to recover and purify the polypeptide; if produced intracellularly, the cells must first be lysed before the polypeptide is recovered.

H7TBA62 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of H7TBA62 polynucleotides for use as diagnostic reagents. Detection of a mutated form of H7TBA62 gene associated with a dysfunction will provide a diagnostic tool that can add to or define a diagnosis of a disease or susceptibility to a disease which results from under-expression, over-expression or altered expression of H7TBA62. Individuals carrying mutations in the H7TBA62 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled H7TBA62 nucleotide sequences. Perfectly matched sequences can be distinguished from mismatched duplexes by RNase digestion or by differences in melting temperatures. DNA sequence differences may also be detected by alterations in electophoretic mobility of DNA fragments in gels, with or without denaturing agents, or by direct DNA sequencing. See, e.g., Myers et al.,Science (1985)230:1242. Sequence changes at specific locations may also be revealed by nuclease protection assays, such as RNase and S1 protection or the chemical cleavage method. See Cotton et al.,Proc Natl Acad Sci USA (1985) 85:4397–4401. In another embodiment, an array of oligonucleotides probes comprising H7TBA62 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to infections such as bacterial, fungal, protozoan and viral infections, particularly infections caused by HIV-1 or HIV-2; pain; cancers; anorexia; bulimia asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the H7TBA62 gene by the methods described.

In addition, infections such as bacterial, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of H7TBA62 polypeptide or H7TBA62 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an H7TBA62, in a sample derived from a host are well-known to those of skill in the art. Such assay method include radioimmunoassays, competitive-binding assays, Western Blot analysis and ELISA assays.

Thus in another aspect, the present invention relates to a diagnostic kit for a disease or suspectability to a disease, particularly infections such as bacterial, fungal, protozoan and viral infections, particularly infections caused by HIV-1 or HIV-2; pain cancers; anorexa; bulimia; asthma; Parkinson's disease; acute heart failure; hypotension; hypertension; urinary retention; osteoporosis; angina pectoris; myocardiai infarction; ulcers; asthma; allergies; benign prostatic hypertrophy, and psychotic and neurological disorders, including anxiety, schizophrenia, manic depression, delirium, dementia, severe medal retardation and dyskinesias, such as Huntington's disease or Gilles dela Tourett's syndrome, which comprises:

(a) a H7TBA62 polynucleotide, preferably the nucleotide sequence of SEQ ID NO: 1, or a fragment thereof;
(b) a nucleotide sequence complementary to that of (a);
(c) a H7TBA62 polypeptide, preferably the polypeptide of SEQ ID NO: 2, or a fragment thereof; or
(d) an antibody to a H7TBA62 polypeptide, preferably to the polypeptide of SEQ ID NO: 2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the H7TBA62 polypeptides. The term "immunospecific" means that the antibodies have substantiall greater affinity for the polypeptides of the invention than their affinity for other related polypeptides in the prior art.

Antibodies generated against the H7TBA62 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kobler, G. and Milstein, C., *Nature* (1975) 256:495–497), the trioma technique, the human B-cell hybridoma technique Kozbor et al., *Immunology Today* (1983) 4:72) and the EBV-hybridoma technique (Cole et al, *MONOCLONAL ANTIBODIES AND CANCER THERAPY,* pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against H7TBA62 polypeptides may also be employed to treat infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia severe metal retardation and dyskinesias, such as Huntington's disease or Gilles dela Tourett's syndrome, among others.

Vaccines

Another aspect of the invention relates to a method for inducing an immunological response in a mammal which comprises inoculating the mammal with H7TBA62 polypeptide, or a fragment thereof, adequate to produce antibody and/or T cell immune response to protect said animal from infections such as bacterial, fungal, protozoan and viral infections, particularly infections caused by HIV-1 or HIV-2; pain cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises, delivering H7TBA62 polypeptide via a vector directing expression of H7TBA62 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a H7TBA62 polypeptide wherein the composition comprises a H7TBA62 polypeptide or H7TBA62 gene. The vaccine formulation may further comprise a suitable carrier. Since H7TBA62 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The H7TBA62 polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al, *Current Protocols in Immunolog* 1(2):Chapter 5 (1991).

H7TBA62 polypeptides are responsible for many biological functions, including many pathologies. Accordingly, it is desirous to find compounds and drugs which stimulate H7TBA62 on the one hand and which can inhibit the function of H7TBA62 on the other hand. In general, agonists are employed for therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy;, and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

In general, such screening procedures involve producing appropriate cells which express the receptor polypeptide of the present invention on the surface thereof. Such cells include cells from mammals, yeast Drosophila or *E coli*. Cells expressing the receptor (or cell membrane containing the expressed receptor) are then contacted with a test compound to observe binding, or stimulation or inhibition of a functional response.

One screening technique includes the use of cells which express receptor of this invention (for example, transfected CHO cells) in a system which measures extracellular pH or intracellular calcium changes caused by receptor activation. In this technique, compounds may be contacted with cells expressing the receptor polypeptide of the present invention. A second messenger response, e.g., signal transduction, pH changes, or changes in calcium level, is then measured to determine whether the potential compound activates or inhibits the receptor.

Another method involves screening for receptor inhibitors by determining inhibition or stimulation of receptor-mediated cAMP and/or adenylate cyclase accumulation. Such a method involves transfecting a eukaryotic cell with the receptor of this invention to express the receptor on the cell surface. The cell is then exposed to potential antagonists in the presence of the receptor of this invention. The amount of cAMP accumulation is then measured. If the potential antagonist binds the receptor, and thus inhibits receptor binding, the levels of receptor-mediated cAMP, or adenylate cyclase, activity will be reduced or increased.

Another method for detecting agonists or antagonists for the receptor of the present invention is the yeast based technology as described in U.S. Pat. No. 5,482,835.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Further, the assays may simply comprise the steps of mixing a candidate compound with a solution containing a H7TBA62 polypeptide to form a mixture, measuring H7TBA62 activity in the mixture, and comparing the H7TBA62 activity of the mixture to a standard.

The H7TBA62 cDNA, protein and antibodies to the protein may also be used to configure assays for detecting the effect of added compounds on the production of H7TBA62 mRNA and protein in cells. For example, an ELISA may be constructed for measuring secreted or cell associated levels of H7TBA62 protein using monoclonal and polyclonal antibodies by standard methods known in the art, and this can be used to discover agents which may inhibit or enhance the production of H7TBA62 (also called antagonist or agonist, respectively) from suitably manipulated cells or tissues. Standard methods for conducting screening assays are well understood in the art.

Examples of potential H7TBA62 antagonists include antibodies or, in some cases, oligonucleotides or proteins which are closely related to the ligand of the H7TBA62, e.g., a fragment of the ligand, or small molecules which bind to the receptor but do not elicit a response, so that the activity of the receptor is prevented.

Thus in another aspect, the present invention relates to a screening kit for identifying agonists, antagonists, ligands, receptors, substrates, enzymes, etc. for H7TBA62 polypeptides; or compounds which decrease or enhance the production of H7TBA62 polypeptides, which comprises:

(a) a H7TBA62 polypeptide, preferably that of SEQ ID NO:2;

(b) a recombinant cell expressing a H7TBA62 polypeptide, preferably that of SEQ ID NO:2;

(c) a cell membrane expressing a H7TBA62 polypeptide; preferably that of SEQ ID NO: 2; or (d) antibody to a H7TBA62 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating an abnormal conditions related to both an excess of and insufficient amounts of H7TBA62 activity.

If the activity of H7TBA62 is in excess, several approaches are available. One approach comprises administering to a subject an inhibitor compound (antagonist) as hereinabove described along with a pharmaceutically acceptable carrier in an amount effective to inhibit activation by blocking binding of ligands to the H7TBA62, or by inhibiting a second signal, and thereby alleviating the abnormal condition.

In another approach, soluble forms of H7TBA62 polypeptides still capable of binding the ligand in competition with endogenous H7TBA62 may be administered. Typical embodiments of such competitors comprise fragments of the H7TBA62 polypeptide.

In still another approach, expression of the gene encoding endogenous H7TBA62 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al, *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of H7TBA62 and its activity, several approaches are also available. One approach comprises administering to a subject a therapeutically effective amount of a compound which activates H7TBA62, i.e., an agonist as described above, in combination with a pharmaceutically acceptable carrier, to thereby alleviate the abnormal condition. Alternatively, gene therapy may be employed to effect the endogenous production of H7TBA62 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publisher Ltd (1996).

Formulation and Administration

Peptides, such as the soluble form of H7TBA62 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0. 1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptdes used in treatment can also be generated endogenously in the subject, in treatment modalities often referred to as "gene therapy" as described above. Thus, for example, cells from a subject may be a engineered with a polynucleotide, such as a DNA or RNA, to encode a polypeptide ex vivo, and for example, by the use of a retroviral plasmid vector. The cells are then introduced into the subject.

EXAMPLE 1

Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insert into a pCDN or pCDNA3 vector. The cells are transfected with individual receptor cDNAs by lipofectin and selected in the presence of 400 mg/ml G418. After 3 weeks of selection, individual clones are picked and for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

EXAMPLE 2

Ligand bank for binding and functional assays

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

EXAMPLE 3
Ligand Binding Assays

Ligand binding assays provide a direct method for ascertaining receptor pharmacology and are adaptable to a high throughout format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

EXAMPLE 4
Functional Assay in Xenopus Oocytes

Capped RNA transcripts from linearized plasmid templates encoding the receptor cDNAs of the invention are synthesized in vitro with RNA polymerase in accordance with procedures. In vitro transcripts are suspended in water at a final concentration of 0.2 mg/ml. Ovarian lobes are removed from adult female toads, Stage V defolliculated oocytes are obtained, and RNA transcripts (10 n/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

EXAMPLE 5
Microphysiometric Assays

Activation of a wide variety of secondary messenger systems results in extrusion of small amounts of acid from a cell. The acid formed is largely as a result of the increased metabolic activity required to fuel the intracellular signal process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

EXAMPLE 6
Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is isolated and identified.

EXAMPLE 7
Calcium and cAMP Functional Assays

7TM receptors which are expressed in HEK 293 cells have been shown to be coupled functionlly to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day>150 selected ligands or tissue/cell extracts are for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence corresponding to nucleotides 1020–2141 of the polynucleotide sequence set forth in SEQ ID NO:1.

2. An isolated polynucleotide comprising the polynucleotide sequence set forth in SEQ ID NO:1.

3. An isolated polynucleotide comprising a nucleotide sequence encoding a polypeptide having the amino acid sequence set forth in SEQ ID NO:2.

4. The isolated polynucleotide of claim 3, wherein said polynucleotide is an RNA sequence corresponding to the entire length of SEQ ID NO:1.

5. The isolated polynucleotide of claim 3 wherein said polynucleotide is an RNA sequence corresponding to nucleotides 1020–2141 of SEQ ID NO:1.

6. An isolated polynucleotide obtained by screening an appropriate library under stringent hybridization conditions with a probe having the sequence of a polynucleotide encoding a polypeptide having the amino acid sequence set forth in SEQ ID NO:2.

7. The isolated polynucleotide of claim 6 wherein the probe comprises the nucleotide sequence set forth in SEQ ID NO:1.

8. An isolated polynucleotide comprising a nucleotide sequence encoding at least 15 contiguous amino acids from the amino acid sequence set forth in SEQ ID NO:2.

9. The isolated polynucleotide of claim 8 comprising a nucleotide sequence encoding at least 30 contiguous amino acids from the amino acid sequence set forth in SEQ ID NO:2.

10. The isolated polynucleotide of claim 8 comprising a nucleotide sequence encoding at least 50 contiguous amino acids from the amino acid sequence set forth in SEQ ID NO:2.

11. The isolated polynucleotide of claim 8 comprising a nucleotide sequence encoding at least 100 contiguous amino acids from the amino acid sequence set forth in SEQ ID NO:2.

12. The isolated polynucleotide of claim 8 comprising a nucleotide sequence encoding at least 200 contiguous amino acids from the amino acid sequence set forth in SEQ ID NO:2.

13. An isolated polynucleotide which is complementary to the polynucleotide sequence set forth in SEQ ID NO:1.

14. An expression vector comprising a polynucleotide encoding a polypeptide comprising at least 50 contiguous amino acids from the amino acid sequence set forth in SEQ ID NO:2.

15. An isolated host cell comprising the expression vector of claim 14.

16. A process for expressing a polypeptide comprising at least 50 contiguous amino acids from the amino acid sequence set forth in SEQ ID NO:2 comprising culturing the host cell of claim 15 under conditions sufficient for the expression of said polypeptide.

17. The process of claim 16 wherein said polypeptide is expressed at the surface of said cell.

18. The process of claim 16 which further includes recovering said polypeptide from the culture.

19. A process for producing a cell which expresses a polypeptide comprising at least 50 contiguous amino acids from the amino acid sequence set forth in SEQ ID NO:2 comprising transforming or transfecting a host cell with the expression vector of claim 14 such that the host cell, under appropriate culture conditions, expresses said polypeptide.

20. Cells produced by the process of claim 19.

21. An expression vector comprising a polynucleotide encoding a polypeptide comprising at least 100 contiguous amino acids from the amino acid sequence set forth in SEQ ID NO:2.

22. An isolated host cell comprising the expression vector of claim 21.

23. A process for expressing a polypeptide comprising at least 100 contiguous amino acids from the amino acid sequence set forth in SEQ ID NO:2 comprising culturing the host cell of claim 22 under conditions sufficient for the expression of said polypeptide.

24. The process of claim 23 wherein said polypeptide is expressed at the surface of said cell.

25. The process of claim 23 which further includes recovering said polypeptide from the culture.

26. A process for producing a cell which expresses a polypeptide comprising at least 100 contiguous amino acids from the amino acid sequence set forth in SEQ ID NO:2 comprising transforming or transfecting a host cell with the expression vector of claim 21 such that the host cell, under appropriate culture conditions, expresses said polypeptide.

27. Cells produced by the process of claim 26.

28. An expression vector comprising a polynucleotide encoding a polypeptide having the amino acid sequence set forth in SEQ ID NO:2.

29. An isolated host cell comprising the expression vector of claim 28.

30. A process for expressing a polypeptide comprising the amino acid sequence set forth in SEQ ID NO:2 comprising culturing the host cell of claim 29 under conditions sufficient for the expression of said polypeptide.

31. The process of claim 30 wherein said polypeptide is expressed at the surface of said cell.

32. The process of claim 30 which further includes recovering said polypeptide from the culture.

33. A process for producing a cell which expresses a polypeptide comprising the amino acid sequence set forth in SEQ ID NO:2 comprising transforming or transfecting a host cell with the expression vector of claim 28 such that the host cell, under appropriate culture conditions, expresses said polypeptide.

34. Cells produced by the process of claim 33.

35. An isolated polynucleotide wherein said polynucleotide is complementary to a nucleotide sequence corresponding to nucleotides 1020–2141 of the polynucleotide sequence set forth in SEQ ID NO:1.

36. An isolated polynucleotide wherein said polynucleotide is complementary to the nucleotide sequence that encodes the polypeptide of SEQ ID NO:2.

* * * * *